United States Patent [19]

Hess et al.

[11] Patent Number: 5,030,670

[45] Date of Patent: Jul. 9, 1991

[54] STABLE AQUEOUS DISPERSIONS OF TETRAALKYLPIPERIDINES

[75] Inventors: Erwin Hess, Aesch; Rainer Wolf, Allschwil, both of Switzerland

[73] Assignee: Sandoz Ltd., Basel, Switzerland

[21] Appl. No.: 254,516

[22] Filed: Oct. 6, 1988

Related U.S. Application Data

[62] Division of Ser. No. 722,311, Apr. 11, 1985, Pat. No. 4,780,494.

[51] Int. Cl.[5] .................. C07D 491/10; C07D 405/04; C08K 5/34; C08L 20/00
[52] U.S. Cl. ........................................ 524/99; 524/91; 524/100; 524/102; 525/162; 525/182; 525/443; 525/540; 546/19
[58] Field of Search .................. 524/99, 91, 100, 102; 525/162, 182, 443, 540; 428/460; 546/19

[56] References Cited

U.S. PATENT DOCUMENTS 4,408,051 10/1983 Hinsken et al. ................ 546/19
4,426,472  1/1984 Berner ............................ 524/99

Primary Examiner—John Kight, III
Assistant Examiner—P. Hampton-Hightower
Attorney, Agent, or Firm—Gerald D. Sharkin; Richard E. Vila; Thomas C. Doyle

[57] ABSTRACT

An aqueous dispersion comprising one or more 2,2,6,6-tetraalkylpiperidine compounds having a molecular weight 2000 or less than 2000 and a melting point of 100° C. or more, one or more cationic, non-ionic and/or anionic dispersing agents and an aqueous medium. These dispersions are suitable for use as light stabilizers in aqueous systems.

32 Claims, No Drawings

STABLE AQUEOUS DISPERSIONS OF TETRAALKYLPIPERIDINES

This is a division of application Ser. No. 06/722,311, filed Apr. 11, 1985, now U.S. Pat. No. 4,780,494.

The invention relates to stable aqueous dispersions of 2,2,6,6-tetraalkylpiperidines and to their use alone or with further stabilisers for light stabilisation of aqueous systems.

2,2,6,6-tetraalkylpiperidine compounds are known. They have up till now been used only in solid or liquid systems employing conventional organic solvents.

However, stable aqueous dispersions of these 2,2,6,6-tetraalkylpiperidine compounds are not known. Indeed, due to their basic amine structure 2,2,6,6-tetraalkylpiperidine compounds would not be expected to form stable dispersions.

Surprisingly, however, it has been found that certain 2,2,6,6-tetraalkylpiperidine compounds can form a stable dispersion in an aqueous medium.

According to the invention there is provided an aqueous dispersion comprising one or more 2,2,6,6-tetraalkylpiperidine compounds having a molecular weight not greater than 2000 and a melting point of 100° C. or more, one or more cationic, non-ionic and/or anionic dispersing agents and an aqueous medium.

Preferred 2,2,6,6-tetraalkylpiperidine compounds are spirocyclic compounds, preferably compounds of formula I

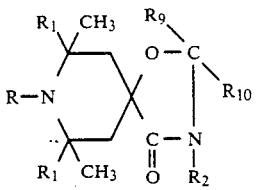

(I)

or are compounds of formula II

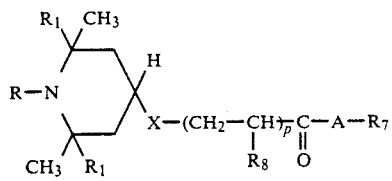

(II)

in which

R is hydrogen, $C_{1-8}$alkyl,

or cyanomethyl;

each $R_1$ independently is —$CH_3$ or —$CH_2(C_{1-4}alkyl)$;

$R_2$ is hydrogen or

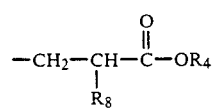

$R_3$ is $C_{1-6}$alkyl, phenyl,

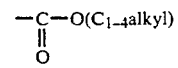

or —$NR_5R_6$;

$R_4$ is a $C_{1-12}$alkyl or $C_{2-12}$alkenyl group which may be unsubstituted or monosubstituted by phenyl or naphthyl and which may be interrupted by oxygen or by a $C_{1-4}$alkylimine group; phenyl; $C_{5-6}$cycloalkyl unsubstituted or substituted by 1 to 3 $C_{1-4}$alkyl groups preferably by 1 or 2 $C_{1-4}$alkyl groups; or $C_{2-20}$alkyl or $C_{2-20}$alkenyl which may be interrupted by oxygen or by a $C_{1-4}$alkylimine group and which is substituted by 1 or 2 groups of formula (a)

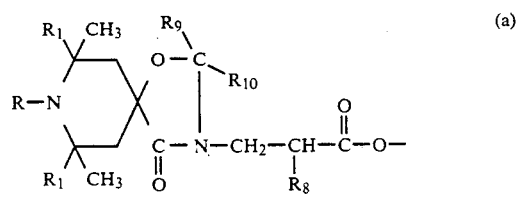

(a)

$R_5$ is hydrogen, $C_{1-12}$alkyl, $C_{5-6}$cycloalkyl, phenyl or ($C_{1-12}$alkyl)phenyl;

$R_6$ is $C_{1-12}$alkyl or hydrogen; or $R_5$ and $R_6$ together with the N-atom to which they are attached form a 5 to 7-membered ring which may contain an additional N- or O-atom (preferably forming a piperidine or morpholine ring);

$R_7$ is

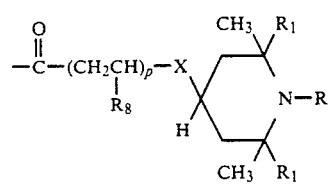

or hydrogen p is 0 or 1;

$R_8$ is hydrogen or methyl;

$R_9$ and $R_{10}$, independently of one another, are hydrogen, $C_{1-30}$alkyl or benzyl; or $R_9$ is hydrogen or $C_{1-4}$alkyl and $R_{10}$ is phenyl, $C_{1-4}$alkylphenyl, chlorophenyl, 4-hydroxy-3,5-ditert.-butylphenyl or naphthyl; or $R_9$ and $R_{10}$ together with the C-atom which they are attached form a $C_{5-15}$cycloalkylidine ring unsubstituted or substituted by a $C_{1-4}$alkyl group or $R_9$ and $R_{10}$ together with the C-atom to which they are attached form a group of formula (b)

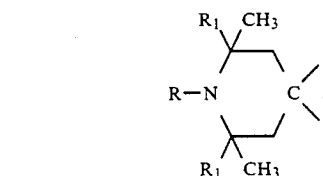

(b)

X is —O— or —NH—

A is $\dfrac{}{}(CH_2)_n$ or

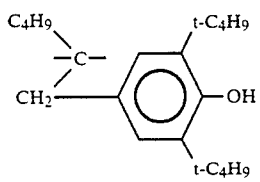

and n is an integer from 0 to 12 inclusive; provided that
1) the molecular weight of the compound of formula I or II is not greater than 2000; and
2) that the melting point is 100° C. or more.

Unless indicated to the contrary where a symbol appears in a formula more than once its significances are independent of one another.

Any phenyl or $C_{5-6}$cycloalkyl present unless otherwise specifically defined is unsubstituted or substituted by 1 to 3 substituents selected from halogen, $C_{1-6}$alkyl or —OH provided only one substituent is —OH or halogen. Any alkyl, alkenyl or alkoxy group capable of being linear or branched is linear or branched unless indicated to the contrary.

To avoid doubt by the term $C_{1-4}$alkylimine is meant

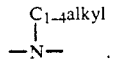

Preferably halogen is Cl or Br, more preferably Cl.
Preferably R is R' where R' is hydrogen, —CH$_3$ or

where R$_3$' is defined below.
Preferably each R$_1$ is —CH$_3$.
Preferably R$_2$ is R$_2$' where R$_2$' is hydrogen or

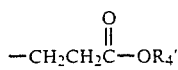

where R$_4$' is defined below.
Preferably R$_3$ is R$_3$' where R$_3$' is $C_{1-6}$alkyl, phenyl, —NR$_5$'R$_6$' or

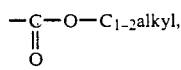

where R$_5$' and R$_6$' are defined below.
Preferably R$_4$ is R$_4$' is $C_{1-8}$alkyl or $C_{5-6}$cycloalkyl substituted by one or two $C_{1-4}$alkyl groups.
Preferably R$_5$ is R$_5$' where R$_5$' is hydrogen, $C_{1-6}$alkyl, $C_{5-6}$cycloalkyl, phenyl unsubstituted or substituted by a $C_{1-6}$alkyl group and
R$_6$ is R$_6$' where R$_5$' $C_{1-4}$alkyl or hydrogen; or
R$_5$' and R$_6$' together with the N-atom to which they are attached form an unsubstituted morpholine or unsubstituted piperidine ring.
R$_7$ is preferably R$_7$' where R$_7$' is

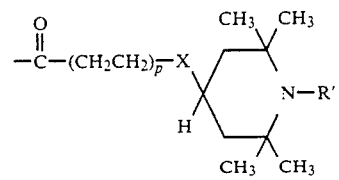

R$_8$ is preferably hydrogen.
Preferably R$_9$ and R$_{10}$ are R$_9$' and R$_{10}$' where R$_9$' and R$_{10}$' together with the C-atom to which they are attached form

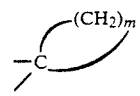

where
m is an interger from 4 to 14 inclusive;
m is preferably m' where m' is 4 to 11, more preferably 11.
Preferred compounds of formula I are of formula Ia

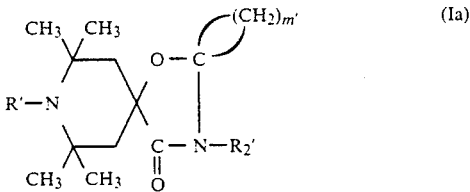

The preparation of aqueous dispersions can be carried out according to conventional methods.

For example the 2,2,6,6-tetraalkylpiperidine compounds can be ground with a dispersing agent in the presence of quarzite beads in a ball mill in water to form a fine dispersion.

Preferably the dispersing agent is one having an HLB-value of at least 10, preferably in the range 15-30.

Compounds of formula (I) and (II) are known or can be made from known compounds by known methods.

Preferred non-ionic dispersing agents are polyalkoxylated aliphatic alcohols, polyalkoxylated alkyl phenols, polyalkoxylated fatty acids and optionally polyalkoxylated mono-, di- and polyglycol ethers. More preferred non-ionic dispersing agents are ethoxylated nonylphenols, ethoxylated i-octylphenols, ethoxylated alkylpolyglycol ethers; ethoxylated dioctylphenols; ethoxylated tridecyl alcohol; dilaurylglycol ethers; and ethoxylated castor oil. The amount of ethoxylation for the above products is preferably 10 to 60, more preferably 10 to 30 for the phenols, 6 to 60 for the polyglycol ethers. The most preferred non-ionic dispersing agents are nonylphenol 15 EO; i-octylphenol 10 or 20 EO; alkyl polyglycol ethers; lauryldiglycol ether; dioctylphenol 30 EO and castor oil 32 EO. EO represents ethylene oxide.

Preferred anionic dispersing agents are sulphonated ditolylether-formaldehyde condensates; sulphonated naphthalene-formaldehyde condensates; ethoxylated and sulphonated novolakcompounds containing at least seven phenyl groups and sulphonated lauryl diglycol ethers. Further preferred anionic dispersing agents are products obtained by carboxymethylation of the alkoxylated non-ionic dispersing agents listed above, particularly carboxymethylated di-iso-octylphenol 30 EO and tridecyl alcohol 6 EO half carboxymethylated. More preferred anionic dispersing agents are the sulphonated ditolylether formaldehyde condensates and the sulphonated napthalene-formaldehyde condensates, most preferably the latter.

Preferred cationic dispersing agents are ethoxylated $R_{12}$—NH—CH$_2$CH$_2$CH$_2$—NH$_2$ where $R_{12}$ is $C_{20-22}$ alkyl; ethoxylated and sulphonated $R_{13}(NH_2)_2$ (where $R_{13}$ is $C_{20-22}$ alkylene); and dimethyl $C_{14}$alkyl benzyl ammonium chloride. More preferred cationic dispersing agents are $R_{12}$—NH—CH$_2$CH$_2$CH$_2$—NH$_2$ 105 EO; the product of $R_{13}(NH_2)_2$ 2 EO and two moles of aminosulphonic acid; and dimethyl $C_{14}$ n-alkylbenzylammonium chloride.

The amount of 2,2,6,6-tetraalkylpiperidine compounds in a dispersion according to the invention is preferably 5 to 50%, more preferably 15 to 40% by weight. The amount of dispersing agent present in a dispersion according to the invention is 2 to 30%, more preferably 3 to 20% based on the amount of 2,2,6,6-tetraalkylpiperidine compound present.

Other stabilisers can be added to and dispersed in a dispersion according to the invention. Such other stabilisers are U.V. absorbers of the oxalanilide series, of the 2-hydroxy-benzophenone series or of the 2-hydroxybenztriazole series. Preferably a dispersion according to the invention includes one or more of such U.V. absorbers.

The dispersion according to the invention can be added simply to aqueous systems by stirring into the system.

By the term aqueous system is meant aqueous emulsions or dispersions of polymeric material, for example those based on acrylic polymers or polyurethanes. Such systems are known for aqueous finishes, "water-borne" systems or dispersion paints. Aqueous systems are described on pages 80 to 96 and 306 to 319 of "Lehrbuch der Lacke und Beschichtungen" Vol. 4 by H. Kittel "Water borne" systems are defined in "Industrie-Lackier-Betrieb" 45 Nr. 2/1977 page 49.

Further, according to the invention there is provided an aqueous lacquer, suitable for use in automotive coatings, comprising an aqueous dispersion of one or more polymeric binders based on thermocrosslinkable acrylic resins, alkyd resins, polyester resins and polyurethane resins, one or more 2,2,6,6-tetraalkylpiperidine compounds having a molecular weight not greater than 2000 and a melting point of 100° C. or more, one or more dispersing agents and an aqueous medium.

Still further according to the invention there is provided a one layer or two layer metallic or non-metallic paint lacquer finish formed from an aqueous lacquer defined above.

Preferred aqueous systems are automotive stoving finishes which heat curable at 85° C. or more.

The aqueous systems according to the invention can be air dried, heat cured or acid catalysed to form the coating.

The amount of a dispersion according to the invention added to an aqueous system is such that the amount of 2,2,6,6-tetraalkylpiperidine compound present (based on dry weight) is 0.1 to 5% of the amount of polymeric material present, more preferably 0.3 to 2%, most preferably 0.5 to 1.5% by weight.

The invention will be illustrated by the following Examples in which all parts and percentages are by weight and all temperatures are in °C.

EXAMPLE 1

120 Parts of the 2,2,6,6-tetraalkylpiperidine compound of formula 1a are mixed with 10 parts of an addition product of 1 mole of i-octylphenol and 10 moles of ethyleneoxide, 270 parts of water and 400 parts of quarzite beads having an average size of 1 to 3 mm. The mixture is finely milled for 4 hours in a ball mill and then filtered from the glass beads. A fine dispersion is obtained in which the compound 1a is present in particle size of 1µ or less.

EXAMPLE 2

The method of Example 1 is repeated except that instead of using 120 parts of the compound 1a a mixture of 40 parts of the compound 1a and 80 parts of a compound of formula 2a is used.

EXAMPLES 3 and 4

Instead of using the 2,2,6,6-tetraalkylpiperidine compound of Examples 1 and 2 an appropriate amount of a 2,2,6,6-tetraalkylpiperidine compound can be used.

APPLICATION EXAMPLE

3 Parts of the dispersion of Example 2 or 4 is added to 100 parts of an acrylate resin dispersion (Neocryl A 622-from Polyvinyl Chemie) having a solid content of 32%. The mixture is formed into a film layer 100µ thick by a doctor blade on a rigid PVC surface and dried at 80° for 10 minutes and then for 16 hours at 50°. The resulting clear transparent film shows very good stability against loss of gloss and cracking when exposed to weathering using a UVCON weathering apparatus (Atlas).

What is claimed is:

1. A method of preparing an aqueous system suitable for use in automotive coatings which comprises adding to an aqueous dispersion or emulsion (A) of a polymeric binder based on a thermocrosslinkable acrylic resin, alkyd resin, polyester resin or polyurethane resin a stable aqueous dispersion (B) comprising (1) at least one 2,2,6,6-tetraalkylpiperidine compound having a molecular weight not greater than 2000 and a melting point of at least 100° C. and being in the form of finely divided particles and (2) a dispersing agent selected from cationic, non-ionic and anionic dispersing agents and mixtures thereof.

2. A method according to claim 1 in which the 2,2,6,6, tetraalkylpiperidine compound is a compound of formula I or II

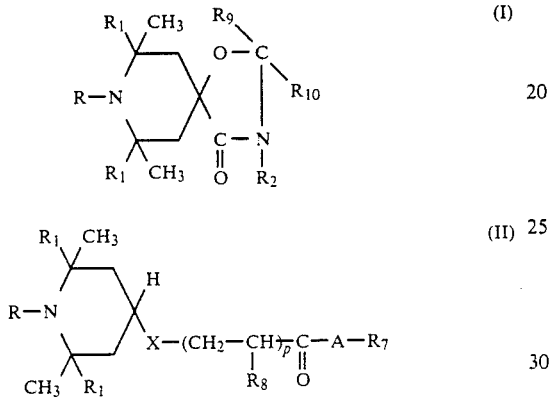

in which

R is hydrogen, $C_{1-8}$alkyl,

or cyanomethyl;

each $R_1$ independently is —$CH_3$ or —$CH_2(C_{1-4}alkyl)$;

$R_2$ is hydrogen or

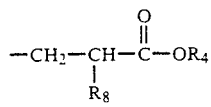

$R_3$ is $C_{1-6}$alkyl, phenyl,

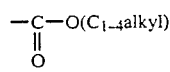

or —$NR_5R_6$;

$R_4$ is a $C_{1-12}$alkenyl group which may be unstituted or monosubstituted by phenyl or naphthyl and which may be interrupted by oxygen or by a $C_{1-4}$alkylimine group; phenyl; $C_{5-6}$cycloalkyl unsubstituted or substituted by 1 to 3 $C_{1-4}$alkyl groups; or $C_{2-20}$alkyl or $C_{2-20}$alkenyl which may be interrupted by oxygen or by a $C_{1-4}$alkylimine group and which is substituted by 1 or 2 groups of formula (a)

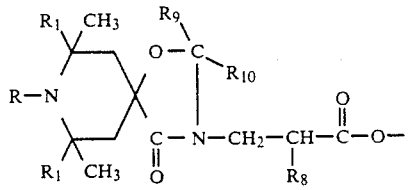

$R_5$ is hydrogen, $C_{1-12}$alkyl, $C_{5-6}$cycloalkyl, phenyl or ($C_{1-12}$alkyl) phenyl;

$R_6$ is $C_{1-12}$alkyl or hydrogen; or $R_5$ and $R_6$ together with the N-atom to which they are attached form a 5 to 7-membered ring which may contain an additional N- or O-atom $R_7$ is

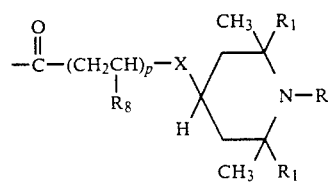

or hydrogen p is 0 or 1;

$R_8$ is hydrogen or methyl;

$R_9$ and $R_{10}$, independently of one another, are hydrogen, $C_{1-30}$alkyl or benzyl; or $R_9$ is hydrogen or $C_{1-4}$alkyl and $R_{10}$ is phenyl, $C_{1-4}$alkylphenyl, chlorophenyl, 4-hydroxy-3,5-ditert.-butylphenyl or naphthyl; or $R_9$ and $R_{10}$ together with the C-atom to which they are attached form a $C_{5-15}$cycloalkylidine ring unsubstituted or substituted by a $C_{1-4}$alkyl group or $R_9$ and $R_{10}$ together with the C-atom to which they are attached form a group of formula (b)

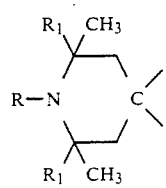

X is —O— or —NH—

A is +$CH_2$+$_n$ or

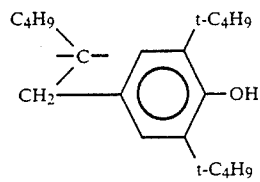

and n is an integer from 0 to 12 inclusive.

3. A method according to claim 2 in which the 2,2,6,6-tetraalkylpiperidine compound is a compound of formula I.

4. A method according to claim 3 in which the 2,2,6,6-tetraalkylpiperidine compound is a compound of formula Ia

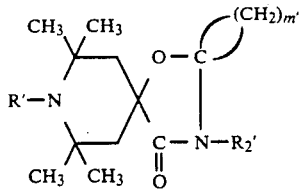 (Ia)

where
R' is hydrogen, —CH$_3$ or

m' is 4 to 11;
R$_2$' is hydrogen or

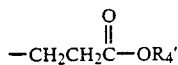

where R$_4$' is defined below;
R$_3$' is C$_{1-6}$alkyl, phenyl, —NR$_5$'R$_6$' or

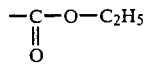

where R$_5$' and R$_6$' are defined below;
R$_4$' is C$_{1-8}$alkyl or C$_{5-6}$cycloalkyl substituted by one or two C$_{1-4}$alkyl groups;
R$_5$' is hydrogen, C$_{1-6}$alkyl, C$_{5-6}$cycloalkyl, phenyl unsubstituted or substituted by a C$_{1-6}$alkyl group; and
R$_6$' is C$_{1-4}$alkyl or hydrogen; or
R$_5$' and R$_6$' together with the N-atom to which they are attached form an unsubstituted morpholine or unsubstituted piperidine ring.

5. A method according to claim 1 in which the non-ionic dispersing agents are selected from polyalkoxylated aliphatic alcohols, polyalkoxylated alkyl phenols, polyalkoxylated fatty acids, and optionally polyalkoxylated mono-, di- and polyglycol ethers; the anionic dispersing agents are selected from carboxymethylation products of the above alkoxylated non-ionic dispersing agents, sulphonated ditolylether-formaldehyde condensates; sulphonated naphthalene-formaldehyde condensates; ethoxylated and sulphonated novolak compounds containing at least seven phenyl groups and sulphonated lauryl diglycol ethers; and the cationic dispersing agents are selected from ethoxylated R$_{12}$—NH—CH$_2$CH$_2$CH$_2$NH$_2$ where R$_{12}$ is C$_{20-22}$alkyl; ethoxylated and sulphonated R$_{13}$(NH$_2$)$_2$ where R$_{13}$ is C$_{20-22}$-alkylene, and dimethylC$_{14}$alkyl benzyl ammonium chloride.

6. A method according to claim 5 in which the non-ionic dispersing agents are selected from ethoxylated nonylphenols, ethoxylated i-octylphenols, ethoxylated alkylpolyglycol ethers; ethoxylated dioctylphenols; ethoxylated tridecyl alcohol, dilaurylglycol ethers; and ethoxylated castor oil; the anionic dispersing agents are selected from sulphonated ditolylether-formaldehyde condensates and the sulphonated naphthalene-formaldehyde condensates; and the cationic dispersing agents are selected from R$_{12}$—NH—CH$_2$CH$_2$CH$_2$—NH$_2$ 105 EO; the product of R$_{13}$(NH$_2$)$_2$ 2 EO and two moles of aminosulphonic acid; and dimethylC$_{14}$ n-alkylbenzyl ammonium chloride, where R$_{12}$ and R$_{13}$ are defined in claim 5.

7. A method according to claim 1 in which the amount of 2,2,6,6-tetraalkylpiperidine compound present, based on dry weight of polymeric material, is 0.1 to 5%.

8. A method according to claim 2 wherein, in the compounds of formulae I and II,
R is R' where R' is hydrogen, —CH$_3$ or

R$_1$ is —CH$_3$,
R$_2$ is R$_2$' where R$_2$' is hydrogen or

R$_3$ is R$_3$' where R$_3$' is C$_{1-6}$alkyl, phenyl, —NR$_5$'R$_6$' or

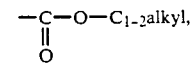

R$_4$ is R$_4$' where R$_4$' is C$_{1-8}$alkyl or C$_{5-6}$cycloalkyl substituted by one or two C$_{1-4}$ alkyl groups,
R$_5$ is R$_5$' where R$_5$' is hydrogen, C$_{1-6}$alkyl, C$_{5-6}$cycloalkyl, phenyl or (C$_{1-6}$alkyl)phenyl,
R$_6$ is R$_6$' where R$_6$' is C$_{1-4}$alkyl or hydrogen, or
R$_5$' and R$_6$' together with the nitrogen atom to which they are attached form an unsubstituted morpholine or unsubstituted piperidine ring,
R$_7$ is R$_7$' where R$_7$' is

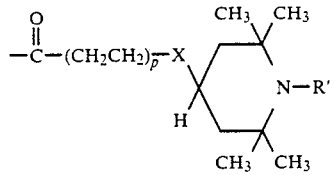

R$_8$ is hydrogen, and
R$_9$ and R$_{10}$ are R$_9$' and R$_{10}$', which, together with the C-atom to which they are attached, form

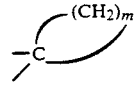

where m is an integer from 4 to 14 inclusive.

9. A method according to claim 1 wherein the dispersing agent has an HLB-value of at least 10.

10. A method according to claim 2 wherein the dispersing agent has an HLB-value in the range of 15-30.

11. A method according to claim 4 wherein the dispersing agent has an HLB-value in the range of 15-30.

12. A method according to claim 5 wherein the dispersing agent has an HLB-value of at least 10.

13. A method according to claim 6 wherein the dispersing agent has an HLB-value in the range of 15-30.

14. A method according to claim 2 in which the non-ionic dispersing agents are selected from polyalkoxylated aliphatic alcohols, polyalkoxylated alkyl phenols, polyalkoxylated fatty acids, and optionally polyalkoxylated mono-, di- and polyglycol ethers; the anionic dispersing agents are selected from carboxymethylation products of the above alkoxylated non-ionic dispersing agents, sulphonated ditolylether-formaldehyde condensates, sulphonated naphthalene-formaldehyde condensates, ethoxylated and sulphonated novolak compounds containing at least seven phenyl groups, and sulphonated lauryl diglycol ethers; and the cationic dispersing agents are selected from ethoxylated $R_{12}$—NH—$CH_2CH_2CH_2NH_2$ where $R_{12}$ is $C_{20-22}$alkyl, ethoxylated and sulphonated $R_{13}(NH_2)_2$ where $R_{13}$ is $C_{20-22}$alkylene, and dimethyl$C_{14}$alkyl benzyl ammonium chloride.

15. A method according to claim 4 in which the non-ionic dispersing agents are selected from ethoxylated nonylphenols, ethoxylated i-octylphenols, ethoxylated alkylpolyglycol ethers, ethoxylated dioctyl-phenols, ethoxylated tridecyl alcohol, dilaurylglycol ethers, and ethoxylated castor oil; the anionic dispersing agents are selected from sulphonated ditolylether-formaldehyde condensates and the sulphonated naphthalene-formaldehyde condensates; and the cationic dispersing agents are selected from $R_{12}$—NH—$CH_2CH_2CH_2$—$NH_2$ 105 EO; the product of $R_{13}(NH_2)_2$ 2 EO dimethyl$C_{14}$n-alkylbenzyl ammonium chloride, where $R_{12}$ is $C_{20-22}$alkyl and $R_{13}$ is $C_{20-22}$alkylene.

16. A method according to claim 14 wherein the dispersing agent has an HLB-value of at least 10.

17. A method according to claim 15 wherein the dispersing agent has an HLB-value in the range of 15-30.

18. A method according to claim 1, wherein the amount of 2,2,6,6-tetraalkylpiperidine compound is 5 to 50% by weight of the dispersion (B) and the amount of dispersing agent is 2 to 30% based on the amount of 2,2,6,6-tetraalkylpiperidine compound.

19. A method according to claim 2 wherein the amount of 2,2,6,6-tetraalkylpiperidine compound is 5 to 50% by weight of the dispersion (B) and the amount of dispersing agent is 2 to 30% based on the amount of 2,2,6,6-tetraalkylpiperidine compound.

20. A method according to claim 4 wherein the amount of 2,2,6,6-tetraalkylpiperidine compound is 15 to 40% by weight of the dispersion (B) and the amount of dispersing agent is 3 to 20% based on the amount of 2,2,6,6-tetraalkylpiperidine compound.

21. A method according to claim 9 wherein the amount of 2,2,6,6-tetraalkylpiperidine compound is 5 to 50% by weight of the dispersion (B) and the amount of dispersing agent is 2 to 30% based on the amount of 2,2,6,6-tetraalkylpiperidine compound.

22. A method according to claim 10 wherein the amount of 2,2,6,6-tetraalkylpiperidine compound is 15 to 40% by weight of the dispersion (B) and the amount of dispersing agent is 3 to 20% based on the amount of 2,2,6,6-tetraalkylpiperidine compound.

23. A method according to claim 16 wherein the amount of 2,2,6,6-tetraalkylpiperidine compound is 15 to 40% by weight of the dispersion (B) and the amount of dispersing agent is 3 to 20% based on the amount of 2,2,6,6-tetraalkylpiperidine compound.

24. A method according to claim 1 wherein the 2,2,6,6-tetraalkylpiperidine compound has a particle size of $1\mu$ or less.

25. A method according to claim 2 wherein the 2,2,6,6-tetraalkylpiperidine compound has a particle size of $1\mu$ or less.

26. A method according to claim 16 wherein the 2,2,6,6-tetraalkylpiperidine compound has a particle size of $1\mu$ or less.

27. A method according to claim 23 wherein the 2,2,6,6-tetraalkylpiperidine compound has a particle size of $1\mu$ or less.

28. A method according to claim 17 wherein the amount of 2,2,6,6-tetraalkylpiperidine compound is 0.1 to 5%, based on the dry weight of the polymeric material.

29. A method according to claim 23 in which the amount of 2,2,6,6-tetraalkylpiperidine compound is 0.1 to 5%, based on the dry weight of the polymeric material.

30. A method according to claim 27 in which the amount of 2,2,6,6-tetraalkylpiperidine compound is 0.1 to 5%, based on the dry weight of the polymeric material.

31. A method according to claim 1 in which the tetraalkylpiperidine compound is a compound of the formula

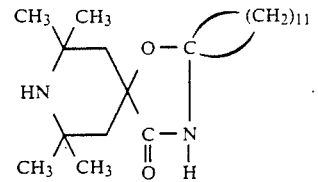

32. A method according to claim 28 in which the tetraalkylpiperidine compound is a compound of the formula

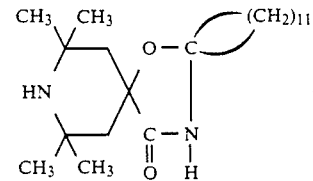

* * * * *